United States Patent
Serhan

(10) Patent No.: US 6,902,568 B2
(45) Date of Patent: Jun. 7, 2005

(54) VERTEBRAL ENDPLATE MILLING DEVICE

(76) Inventor: Hassan Serhan, 27 Forest Edge Rd., South Easton, MA (US) 02375

( * ) Notice: Subject to any disclaimer, the term of this patent is extended or adjusted under 35 U.S.C. 154(b) by 404 days.

(21) Appl. No.: 10/101,104

(22) Filed: Mar. 19, 2002

(65) Prior Publication Data

US 2003/0181915 A1 Sep. 25, 2003

(51) Int. Cl.$^7$ ................................. A61B 17/32
(52) U.S. Cl. ....................................... 606/79
(58) Field of Search .................. 606/79–81, 167, 606/169–170, 180; 408/168, 172, 179

(56) References Cited

U.S. PATENT DOCUMENTS

| | | | |
|---|---|---|---|
| 79,276 A | * 6/1868 | Sullivan | .................... 408/169 |
| 1,202,139 A | * 10/1916 | Witanowski | ................. 408/157 |
| 3,702,611 A | * 11/1972 | Fishbein | ..................... 606/81 |
| 5,445,639 A | 8/1995 | Kuslich | |
| 6,083,228 A | 7/2000 | Michaelson | |
| 6,176,882 B1 | 1/2001 | Harms | |
| 6,224,604 B1 | 5/2001 | Suddaby | |
| 6,726,690 B2 | * 4/2004 | Eckman | ..................... 606/79 |
| 2001/0034526 A1 | 10/2001 | Kuslich | |

OTHER PUBLICATIONS

European Search Report EP03251688 dated Nov. 14, 2003.

* cited by examiner

Primary Examiner—Kevin Shaver
Assistant Examiner—Michael B. Priddy

(57) ABSTRACT

A milling device having in which opposed distance adjustment elements are slidably coupled with two surfaces of the device's abrading element which face away from the abrading surface of the device's abrading element.

46 Claims, 10 Drawing Sheets

VERTEBRAL ENDPLATE MILLING DEVICE

BACKGROUND OF THE INVENTION

Many spinal surgical procedures involve the removal of a problematic intervertebral disc followed by the placement of a prosthetic implant (such as a fusion body, spacer or a motion disk) within the intervertebral disc space.

U.S. Pat. No. 6,083,228 ("Michelson") discloses abrading elements particularly designed for preparing the intervertebral space in the spine for reception of the implant between adjacent vertebral bodies. FIG. 20 of Michelson discloses an abrading device having a pair of parallel abrading elements connected to a rotary drive mechanism which allows for simultaneous preparation of the adjacent endplates. However, the abrading surfaces of Michelson's devices preferably have a leading edge which removes material along that edge as it is advanced into the disk space. See, e.g., FIGS. 17A and 17B of Michelson. Accordingly, the anterior lips of the opposing vertebrae (which helps retain the implant in its desired space) are undesirably removed by the action of this device as the device enters the disc space. See FIG. 19 of Michelson.

When a variation in the height of the disk space must be accommodated, Michelson teaches using an adjustment screw in conjunction with a pair of wedge-shaped blocks, each having a threaded aperture for receiving the adjustment screw. According to Michelson, as the adjustment screw is turned, the wedged-shaped blocks move relative to one another to change the distance between the abrading surfaces. See col. 12, lines 45–57 of Michelson. The exact placement of these wedged-shaped blocks within the device is not explicitly described by Michelson. However, FIG. 20 also discloses a pair of opposed vertically-disposed frusto-conical openings in the center of each abrading element 94 and 96. Accordingly, it appears that Michelson suggests that the wedged-shaped blocks are located in these frustoconcial openings, and that the adjustment screw is vertically-disposed therethrough. Since this vertically-disposed screw must be accessed from either the top or bottom of the device, it does not appear to be accessible to the surgeon once the abrading elements are inserted into the disc space. Accordingly, Michelson's "adjustable screw" device also appears to allow for a height adjustment only before the abrading elements are inserted into the disc space. Since these abrading elements are fixed prior to their entry into the disk space, it is reasonable to conclude that they also remove the anterior lips of the opposing vertebrae as this device is advanced into the disk space.

FIG. 23 of Michelson discloses a vibratory milling device whose abrading elements 218 have rounded working surfaces. Although it appears this device does not remove the anterior lips of the opposing vertebrae, since the device does not provide for in-situ height adjustment, the distance between these elements is fixed during operation, and so these elements must undesirably stretch the ligaments surrounding the disc space as they enter the disc space.

In sum, the devices of FIGS. 17 and 20 of Michelson undesirably eliminate the anterior vertebral lips which help retain the implant, while the device of FIG. 23 undesirably stretches the ligaments surrounding the vertebrae which help retain the implant.

Therefore, there is a need for a milling device which suitably prepare the disc space for the insertion of an implant, while retaining the anterior lips of the opposing vertebrae, but without stretching the vertebral ligaments During endplate preparation, it is often desirable to increase the pressure upon the endplate being prepared in order to reduce preparation time. Michelson teaches one technique for increasing abrading pressure by using a device having an abrading surface on only one side of the device (as in FIG. 2 of Michelson) and using the non-abrading side as a fulcrum. However, the use of a non-abrading surface allows only for single-sided milling, and so doubles the time required for milling.

Michelson teaches sequentially selecting progressively larger abrading elements to form the desired disk space in a step-wise fashion (4, 45–46). The sequential nature of this activity makes for a time-consuming procedure.

In addition, Michelson does not teach measuring annular tension with the disclosed milling devices.

U.S. Pat. No. 5,865,846 ("Bryan") teaches forming concave surfaces of predetermined shape in opposing vertebral endplates. However, the milling device used in such a procedure is not disclosed by Bryan.

U.S. Pat. No. 5,514,180 ("Heggeness") discloses forming spinal prostheses having shapes which conform to the natural contour of the opposing vertebral endplates.

Therefore, there is a need for a milling device suitable for preparing a space in the human spine to receive an insert between adjacent vertebral bodies which can preserve the endplate lips without stretching the ligaments.

SUMMARY OF THE INVENTION

The present invention relates to a milling device in which distance adjustment elements are slidably coupled with two surfaces of the abrading element which face away from the abrading surface. In contrast to the Michelson device (wherein the coupling appears to occur with at least one surface which faces in the same direction as the abrading surface), the distance between the distance adjustment elements of the present invention may be conveniently adjusted from a position lateral to the abrading surface. As that distance is adjusted, the position of the abrading element is correspondingly adjusted to a position higher or lower upon the sliding surfaces of the distance adjustment elements.

Thus, in a device having a pair of abrading surfaces facing opposite directions, the device may be inserted into the disc space in a first closed position having a small profile. Advancement into the disc space with the small profile not only avoids contact with the endplates, but also avoids any stretching of the ligaments. Once the device is safely within the disc space, the distance between the apices of the abrading surfaces may be increased to an open position, thereby creating the desired concave contours upon the endplates without stretching the ligaments.

Therefore, in accordance with the present invention, there is provided a device for preparing a space in the human spine to receive an insert between adjacent vertebral bodies, comprising:
a) a first abrading element comprising:
  i) a first abrading surface shaped to create a first predetermined surface contour in a vertebral body endplate,
  ii) a first surface portion facing away from the first abrading surface, and
  iii) a second surface portion facing away from the first abrading surface,
b) a first distance adjustment element having a first sliding surface contacting the first inner surface portion for slidable engagement therewith, and
c) a second distance adjustment element having a second sliding surface contacting the second inner surface portion for slidable engagement therewith.

DESCRIPTION OF THE FIGURES

FIG. 8b is a cross-section of FIG. 8a.

DETAILED DESCRIPTION OF THE INVENTION

Figure 1:
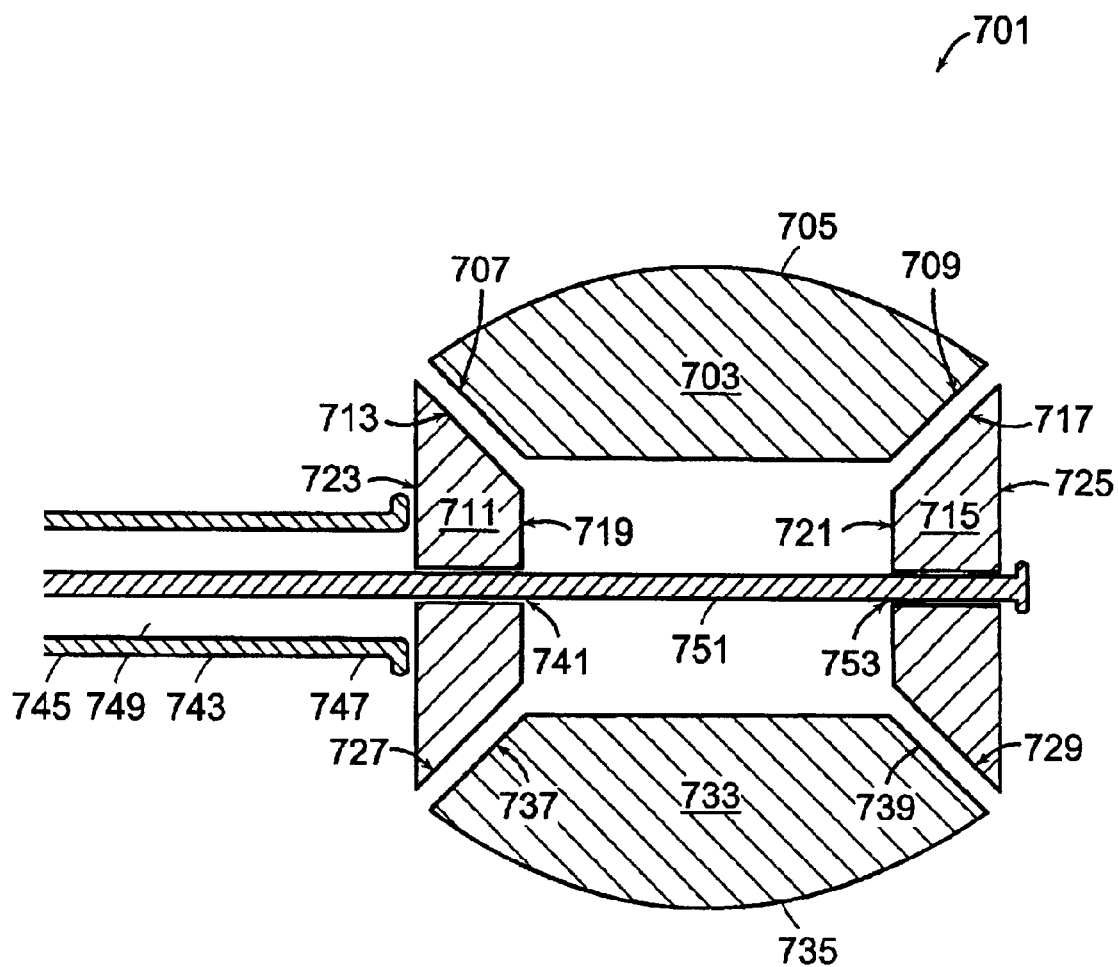
FIG. 1 is a cross-section of a first embodiment of a device of the present invention.

Now referring to FIG. 1, there is provided a device 701 for preparing a space in the human spine to receive an insert between adjacent vertebral bodies, comprising:
a) a first abrading element 703 comprising:
 i) an first abrading surface 705 shaped to create a first predetermined surface contour in a vertebral body endplate,
 ii) a first surface portion 707 facing away from the first abrading surface, and
 iii) a second surface portion 709 facing away from the first abrading surface,
b) a first distance adjustment element 711 having a first sliding surface 713 contacting the first surface portion 707 for slidable engagement therewith, and
c) a second distance adjustment 715 element having a second sliding surface 717 contacting the second inner surface portion 709 for slidable engagement therewith.

Figure 2:
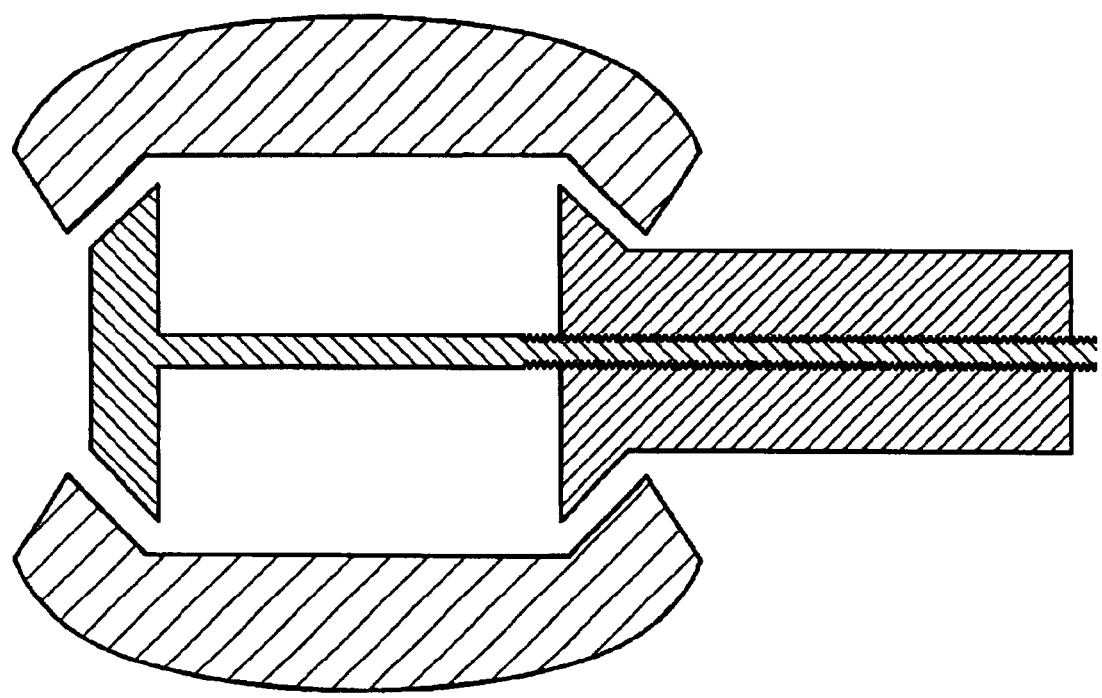
FIG. 2 is a cross-section of an embodiment of the present invention wherein movement of the distance adjustment elements away from each other can increase the height of the device.

The first and second sliding surfaces may be arranged so as to oppose each other, or to face away from each other. For example, in FIG. 1, the first sliding surface 713 opposes the second sliding surface 717. Because these surfaces oppose each other, first abrading element 703 is moved to a position higher upon the sliding surfaces when the distance adjustment elements are moved together. In other embodiments, the first and second sliding surfaces may be arranged so as to face away from each other (as in FIG. 2).

The distance adjustment elements may possess any shape suitable for sliding engagement with a surface portion of an abrading element. For example, the distance adjustment element may have a cross-section of regular geometric shape (such as a parallelogram), or a thin flange. Many embodiments of the distance adjustment elements may conveniently be characterized as a trapezoid possessing parallel inner and outer faces between which reside the sliding surfaces which engage the adjacent abrading elements. For example, in FIG. 1, first distance adjustment element 711 further comprises a first inner face 719, second distance adjustment element 715 further comprises a second inner face 721, and the first inner face opposes the second inner face. First distance adjustment element further comprises a first outer face 723, the second distance adjustment element further comprises a second outer face 725, and the first outer face faces away from the second outer face.

In some embodiments, and particularly those in which the distance adjustment element has a regular geometric shape, through-holes are provided which traverse the inner and outer faces of the distance adjustment element. These holes may be used to help fix the position of elongate members (whose function will be explained below). For example, in FIG. 1, first distance adjustment element further comprises a first hole 741 traversing the inner 719 and outer 723 faces thereof, while the second distance adjustment element 715 further comprises a second hole 753 traversing the inner 721 and outer 725 faces thereof Preferably, the first and second holes are co-axial so that an essentially linear elongate member may be easily occupy each hole.

The distance between the distance adjustment elements may be adjusted by an means. In many embodiments, the adjustment is conveniently performed by using at least one elongate member which extends laterally from the device, thereby allowing the surgeon to perform the desired distance adjustment from outside the disc space while the device is located within the disk space. In many embodiments, first and second elongate members are provided which respectively contact first and second distance adjustment elements. Relative movement of the two elongate members results in a relative movement of the distance adjustment members.

For example, the device of FIG. 1 further comprises a first elongate member 743 having proximal portion 745 and a distal portion 747. The elongate member forms a hollow shaft 749, wherein the distal portion 747 contacts the outer face 723 of the first distance adjustment element 711. The device of FIG. 1 further comprises a second elongate member 751 extending through the hollow shaft 749 and the first hole 741. In this embodiment, the second elongate member 751 is slidably disposed in the first hole 741 and the second hole 753.

In this FIG. 1 embodiment, the first distance adjustment element 711 and the distal portion 747 of the first elongate member are integral.

Figure 3A:
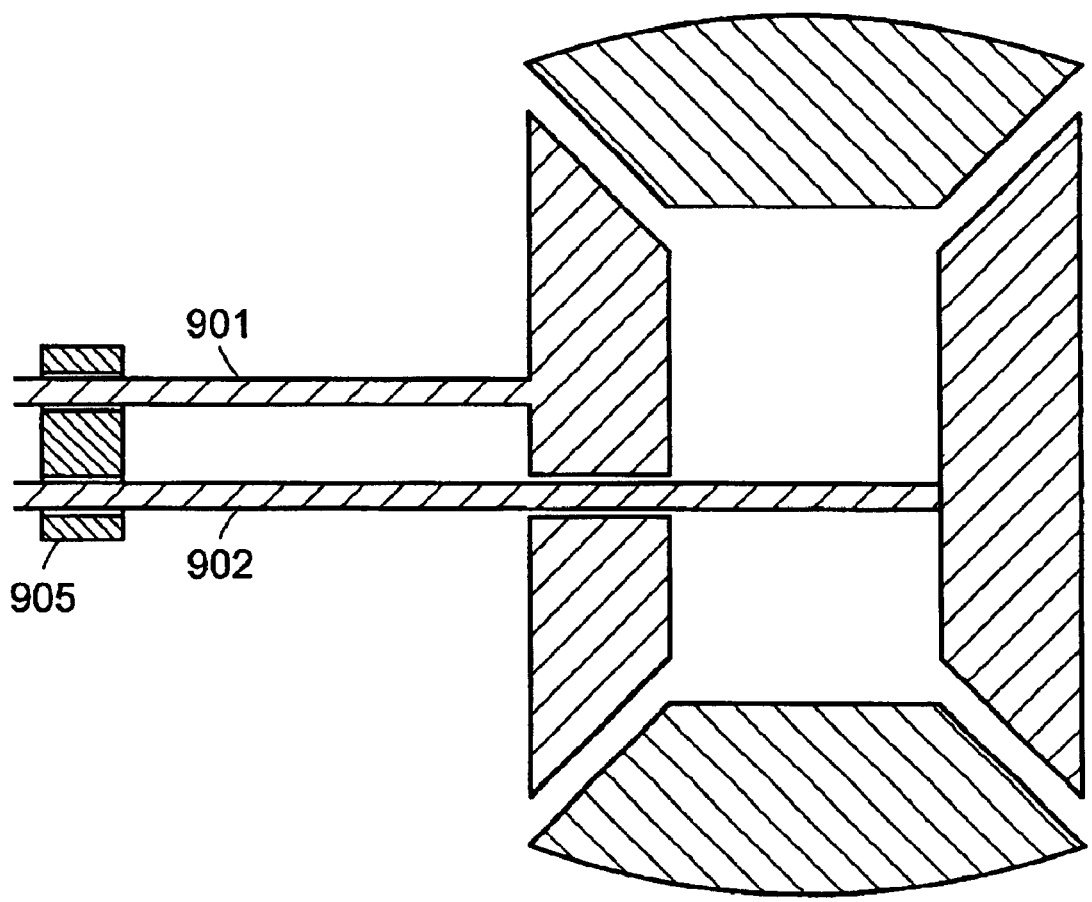
FIG. 3a is a cross-section of a device of the present invention, wherein the elongate members are disposed side-by-side parallel relationship, and are held in place by an outer band.
Figure 3B:
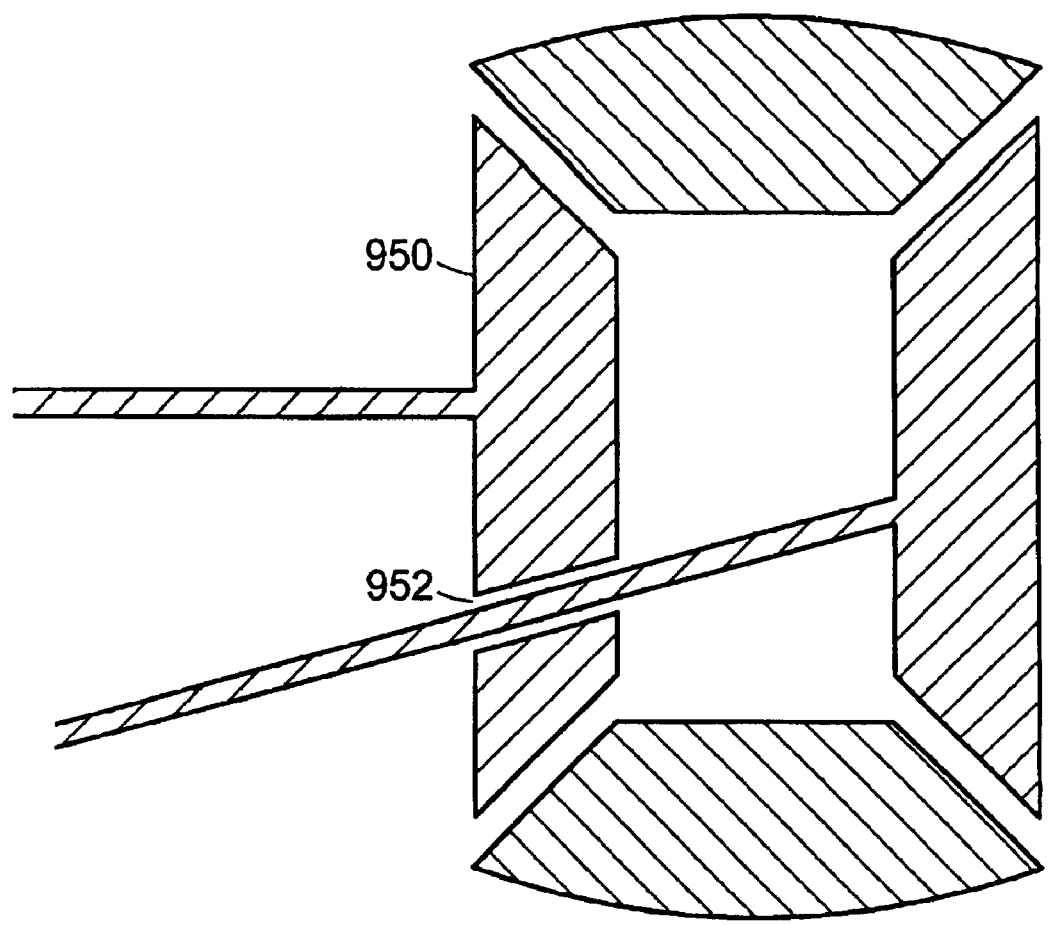
FIG. 3b is a cross-section of a device of the present invention, wherein the elongate members may disposed in a fixed angular relationship fixed by a distance adjustment element having a bore for accommodating an elongate member.

Although many embodiments utilize elongate members in a co-axial relationship, there is no requirement that such members must always be co-axial. For example, in other embodiments, as in FIG. 3a, the elongate members 901 and 902 are disposed side-by-side parallel relationship, and are held in place by an outer band 905. In this embodiment, each elongate member is integral with the corresponding distance adjustment element. In other embodiments, as in FIG. 3b, the elongate members may disposed in a fixed angular relationship fixed by a wedge 950 having at least one bore 952 for accommodating at least one elongate member. In this embodiment the distance adjustment member may act as the wedge.

In some embodiments, the device is designed to work upon two opposing endplates at the same time. In these embodiments, the device may conveniently further comprises an additional abrading element whose abrading surface faces in the direction which is opposite that of the first abrading surface. The device may also comprises two additional distance adjustment elements, each comprising a sliding surfaces adapted to slidably engage the surface portions of the abrading element which face away from the second abrading surface. For example, in FIG. 1, First distance adjustment element further comprises a third sliding surface 727 facing away from the first sliding surface 713, and the second distance adjustment element further comprises a fourth sliding surface 729 facing away from the second sliding surface 717. In this embodiment, the third sliding surface opposes the fourth sliding surface. FIG. 1 also discloses a second abrading element 733 comprising:

i) a second abrading surface 735 shaped to create a second predetermined surface contour in a vertebral body endplate, and ii) a third surface portion 737 facing away from the second abrading surface 735, and iii) a fourth surface portion 739 facing away from the second abrading surface 735, wherein the third surface portion 737 contacts the third sliding surface 727 for slidable engagement therewith, and wherein the fourth surface portion 739 contacts the fourth sliding surface 729 for slidable engagement therewith.

Figure 4A:
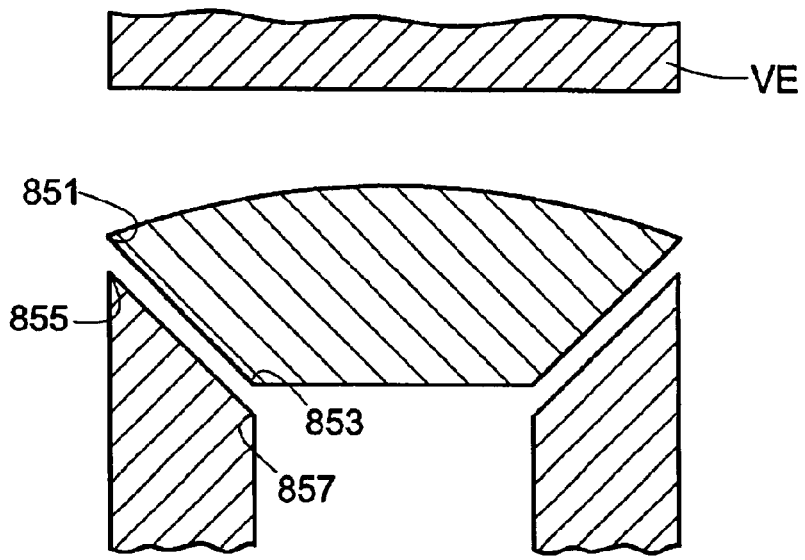
FIGS. 4a and 4b are cross-sections of a portion of the device of the present invention located adjacent a vertebral endplate in its respective closed and open positions, wherein the closed position does not contact an adjacent vertebral endplate and the open position contacts the adjacent vertebral endplate.
Figure 4B:
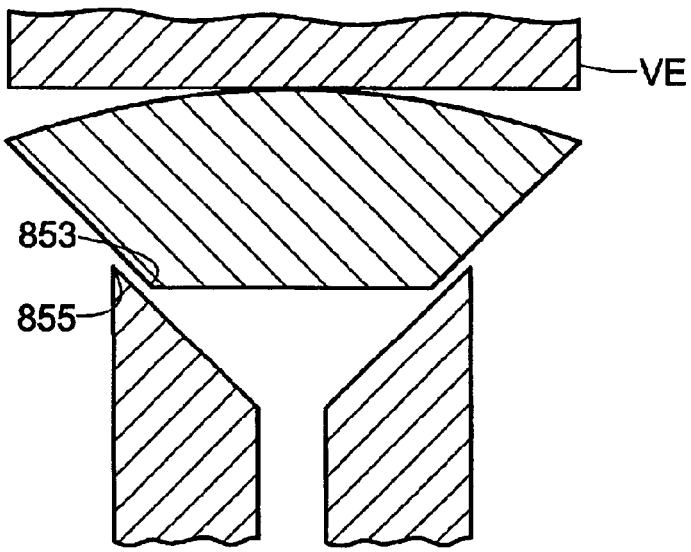

In use, the activation of the device allows the abrading elements to move from a closed position (which is desirable for entering the disc space without unduly streching the surrounding ligaments) to an open position (which is desirable for preparing the endplates. Now referring to FIG. 4a, when the device is outside the disc space and in the closed position, in many embodiments the inner end portion 857 of the sliding surface contacts the inner end portion of the corresponding surface portion 853. In addition, the outer end portion 855 of the sliding surface contacts the outer end portion of the corresponding surface portion 851. Once this device has entered the disc space, it may now be conveniently opened. Now referring to FIG. 4b, the device of FIG. 4a is activated so as to decrease the distance between the distance adjustment elements. As this occurs, the abrading element is pushed upwards into an open position so that the outer end portion 855 of the sliding surface contacts the inner end portion of the corresponding surface portion 853. The resulting height adjustment causes the abrading surface to contact endplate VE.

When elongate members are used, they are typically provided in a configuration that produces in-situ height adjustment of the abraders upon a change in the relative position of the elongate members. Preferably, the elongate members are disposed so that a change in their relative position along their major axes changes the distance between the distance adjustment elements. The change in distance between the distance adjustment elements will then force the abraders which abut the distance adjustment elements either toward the elongate members (to a more closed position) or away from the elongate members (to a more open position), thereby providing the desired in-situ height adjustment capability.

In some embodiments, there is provided a first elongate member and a second hollow elongate member, wherein the first elongate member is slidably disposed within the second hollow elongate member. In these embodiments, the first elongate member may be either solid or hollow. In addition, C-shape elongate members having an essentially hollow interior are also contemplated.

For example, in some embodiments, the elongate members are selected so that a solid rod (the first elongate member) extends distally from a hollow shaft (the second hollow elongate member), as in FIG. 1. In these embodiments, the design and manufacture of the device is relatively simple.

Figure 5:
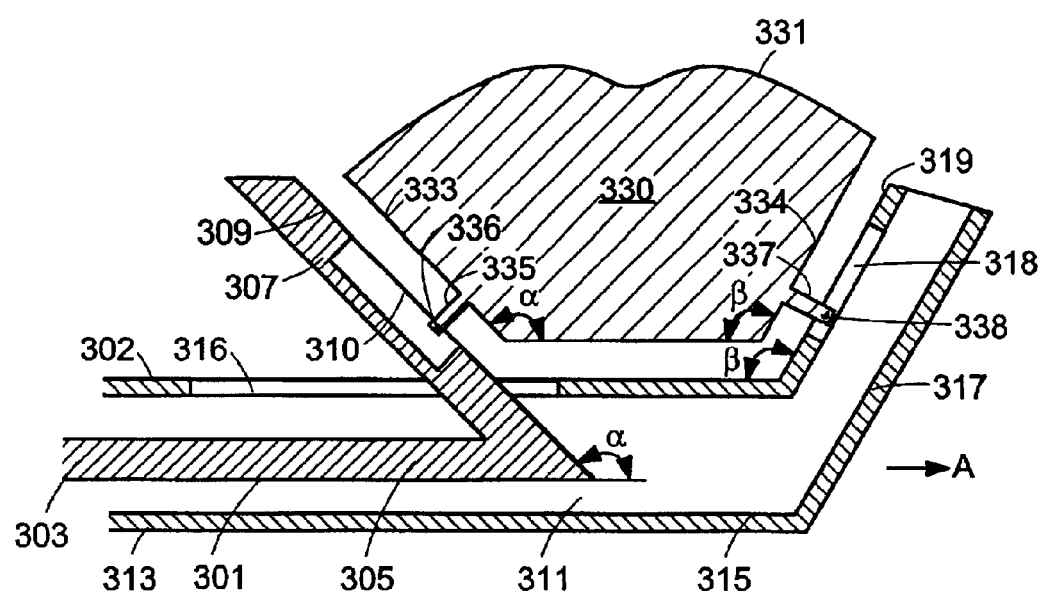
FIG. 5 is a cross-section of a vibratory embodiment of the present invention.

However, in other embodiments, the elongate members are selected so that the solid rod terminates proximally within the hollow shaft, as in FIG. 5. In these embodiments like FIG. 5, the design device typically includes a slot 316 disposed upon the surface of the hollow shaft from which its distance adjustment element extends and running parallel to the longitudinal axis A of the hollow shaft. When so designed, this slot accommodates the desired axial movement of proximal distance adjustment element. Although these embodiments are more complex, they are nonetheless useful.

Preferably, when co-axial elongate members are selected, the inner elongate member is axially movable within the hollow portion of the outer elongate member is also slidably movable along axis A within the outer shaft. When the inner rod is axially movable, the surgeon can easily adjust the relative position of the elongate members by simply slidably moving the inner rod either into or out of the outer hollow shaft.

In some embodiments, other types of axial movement, such as ratcheting, are also contemplated as within the scope of the invention.

Figure 6:
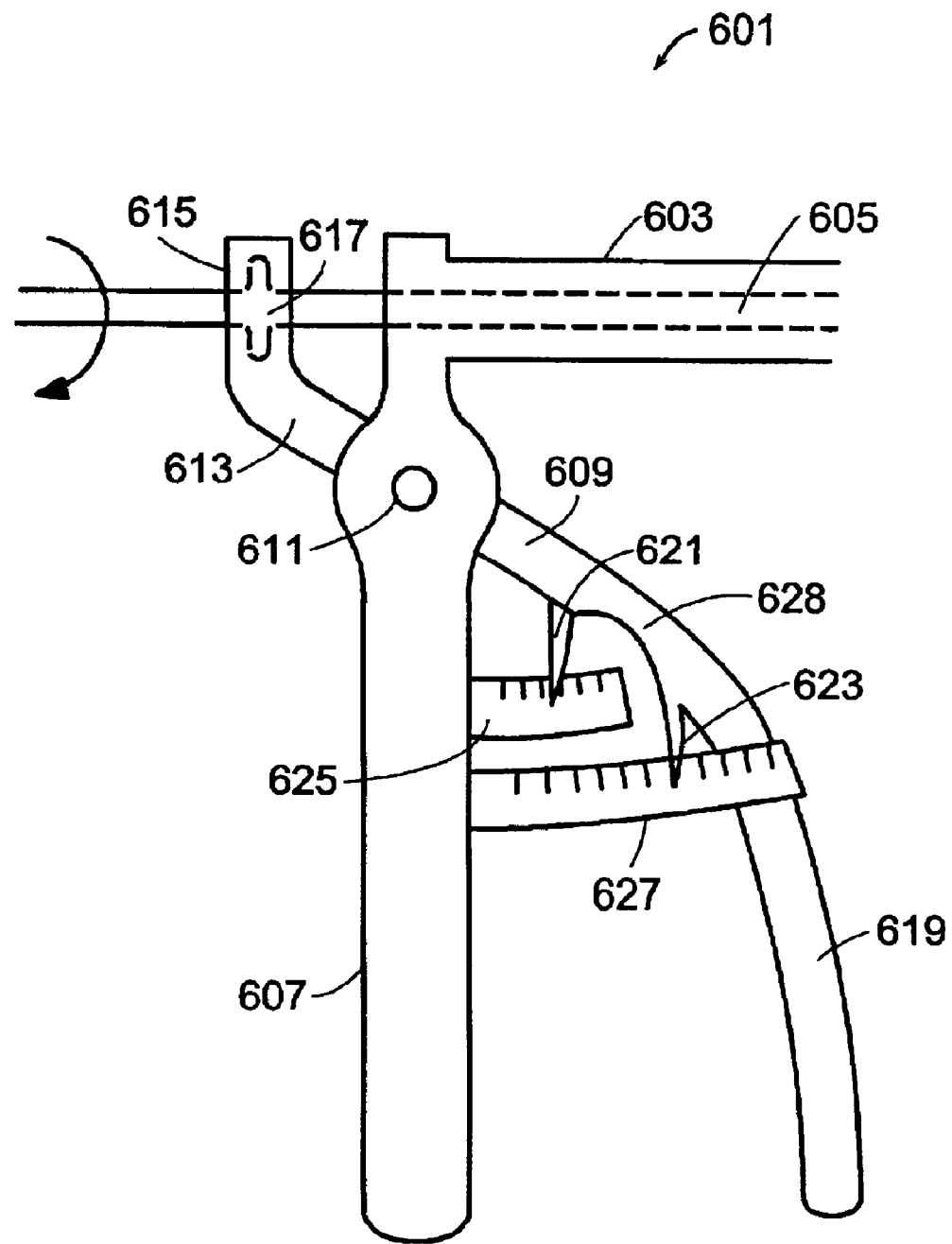
FIG. 6 is a side view of a proximal portion of the present invention having a tension measuring means.

In some embodiments, means for measuring disc height and tension are contemplated as within the scope of the invention. Now referring to FIG. 6, the proximal end 601 of the device may comprise co-axial elongate members comprising a hollow outer elongate member 603 and an inner elongate member 605. The proximal end of the outer elongate member may form a handle 607 for suitable gripping the device. The device may further comprise a trigger 609 pivotally attached to the handle 607 by pivot means 611. In this embodiment, a proximal end portion 613 of the trigger may form a ring 615 which wraps around a portion of the inner elongate member 605 which extends proximally from the hollow outer elongate member 603. In addition, bearing means 617 is provided at the ring—inner elongate member interface to allow for free rotation of the elongate member. As the surgeon the handle and pulls the distal end 619 of trigger 609 towards the handle, inner elongate member is advanced distally.The device of FIG. 6 also includes a pair of measuring means. In particular, trigger 609 includes first 621 and second 623 pointers while handle 607 includes first 625 and second 627 measuring bars having demarcations for measuring the displacement of the inner elongate member. The displacement of pointer 621 allows the surgeon to measure disc height. A portion 628 of the handle located proximal to pointer 623 is relatively narrowed and therefore more susceptible to bending displacement when the trigger is pulled towards the handle. The displacement of this portion is measured by pointer 623 along bar 627, and is a measure of the tension created by the displacement.

Figure 7:
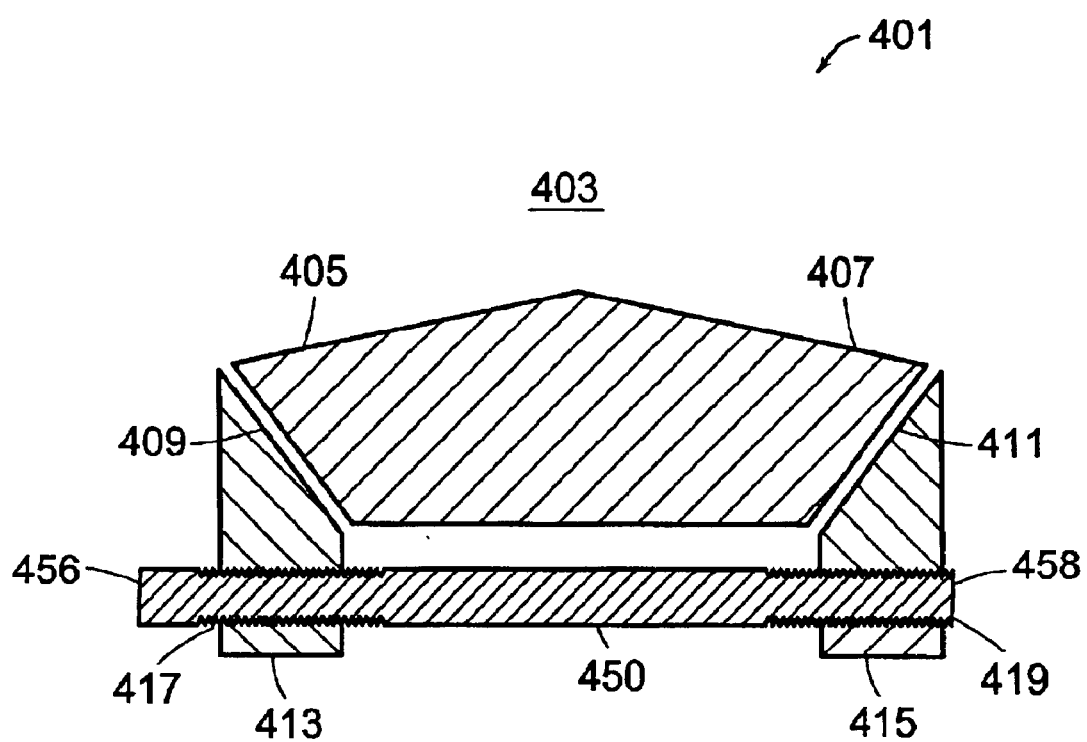
FIG. 7 is an embodiment of the present invention using a elongate member having a reversed thread.

In still other embodiments, as in FIG. 7, in-situ height adjustment is provided by using a screw having opposed reversed threads. In particular, FIG. 7 discloses an adjustable abrader device 401 shaped for insertion between adjacent vertebrae. The device 401 comprises abrading element 403 whose first and second surfaces portions 405, 407 slidably engage the first 409 and second 411 sliding surfaces of distance adjustment elements 413, 415. Each distance adjustment element further has a hole 417, 419 which is threaded in opposing directions. Lastly, an externally threaded screw 450 having opposing reversed threads 456, 458 is disposed within the threaded holes. Distance adjustment elements are generally fixed within a housing (not shown) along a track so that they may move along the A axis, but may not rotate about the screw. Accordingly, rotation of the screw brings the distance adjustment elements closer or farther apart, thereby moving the abrading element into an open or closed position.

Alternatively, a device of the present invention incorporating reversed screw thread technology may also use a threaded nut assembly in the manner disclosed in U.S. Pat. No. 5,658,335, the specification of which is incorporated by reference.

These reversed screw thread embodiments can provide advantage in that they may be constructed with only a single elongate member, can provide a stationary setting, and can be used in vibratory embodiments.

In many embodiments, the abrading surface is substantially convex in at least one plane. The convexity of the abrading surface will produce a desirable concave shape in the vertebral endplate which can securely hold in place a convex-shaped implant. In preferred embodiments, the abrading surface is substantially convex in two planes.

In some embodiments, the abrading surface has a contour suitable for producing a contour in an endplate which can securely hold the motion discs disclosed in U.S. Pat. No. 5,824,094 ("Serhan").

In some embodiments, the abrading surface has at least one feature. When used in conjunction with a non-rotary abrading means (such as a vibratory element), this feature will produce a predetermined relief area in the endplate contour for accommodating a stability-enhancing protrusion present on the surface of the implant.

The abrading element can be driven by any conventional abrading means such as rotary milling means or vibratory milling means. Typically, a device having rotary milling means is preferred when a highly precise contour is desired. However, the utility of rotary milling means is somewhat limited by its ability to produce essentially only circular contours. If a complex contour is desired, then use of a vibratory device is preferred.

If a rotary milling device is selected, then it is preferred than the two distance adjustment elements and the abrading element be adapted to produce a gear mechanism. In such a case, and now referred to FIGS. 8a and 8b, each distance adjustment element comprises a frustoconical gear member 7,9 having a through-hole 41,43 for slidable reception along the axis of a distally extending elongate member 11. Each frustoconical gear member should also possess gear teeth 45,47 disposed circumferentially about its tapered surface. Preferably, the gear teeth are present in the form of grooves running radially with the tapered surface. These grooves will enhance the engagement of the distance adjustment elements to portions of the corresponding frustoconical gear member 49 of the abrading element.

Likewise, the preferred abrading element in a rotary milling device has a frustoconical portion 49 adapted for engaging both of the frustoconical gear members at the same time. The frustoconical portion of the abrading element should also possess gear teeth 51, 53 disposed circumferentially about its tapered surface. Preferably, these gear teeth are also present in the form of grooves running radially with the tapered surface, as these grooves will enhance the engagement of the frustocone to the frustocone gear members.

If a rotary milling is desired, it is preferred that the angle α formed by the frustocone surface (in relation to the longitudinal axis A of the elongate members) be between 30 and 60 degrees. When rotary milling is desired, one of the frustoconical gear members may preferably be integrally bound to the distally extending elongate member so that rotation of the rod will turn the frustoconical gear member is a desired direction. Accordingly, the distally extending rod will preferably pass through the through-hole of the non-integrated (i.e., free) gear member so that this latter free gear member can freely rotate in the opposite direction of the integrated gear member and move along axis A in response to pull on the rod. The axial movement of this free gear member resulting from the proximal pulling of the inner elongate member brings the gears closer together, thereby forcing the abrading element away from the inner rod due to the frustoconical nature of the engagement surfaces.

Figure 8A:
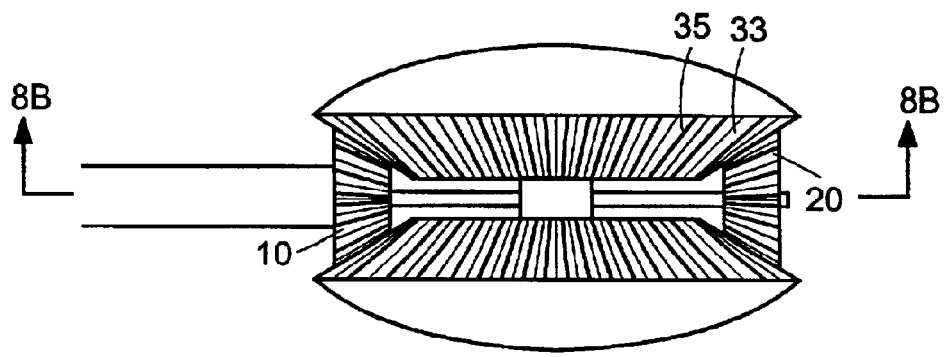
FIG. 8a is a side view of a rotary embodiment of the device of the present invention.
Figure 8B:
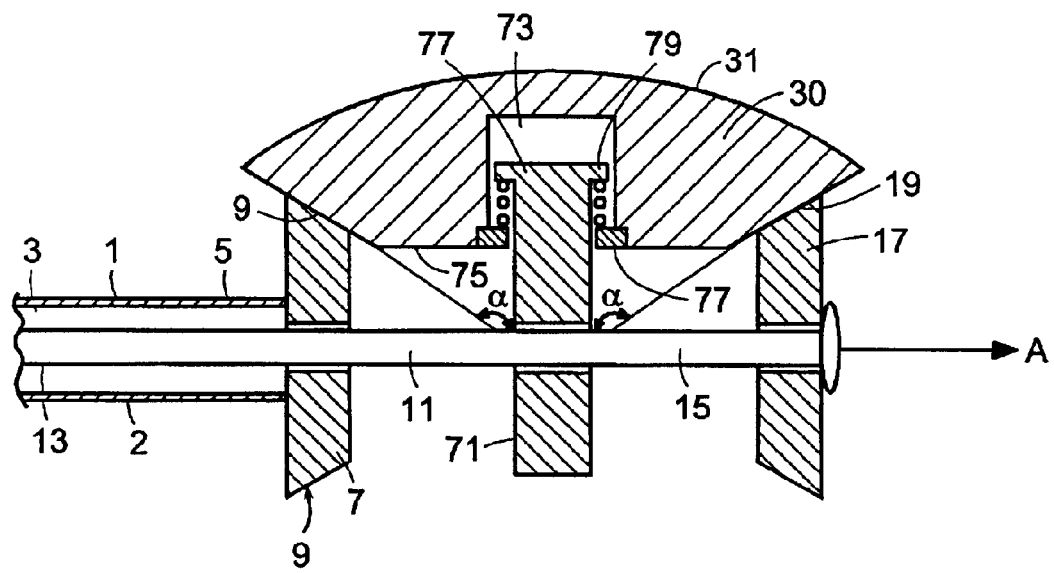

In other embodiments, as in FIG. 8b, the proximal gear member 7 is integrally connected to the inner elongate member 11 while the distal gear member 17 is slidably received on the inner elongate member 11. When the inner elongate member 11 is pulled proximally, the proximal gear remains stationary while the distal gears slides proximally along the inner elongate member 11, thereby reducing the distance between the gears and causing the abrading surface to rise away from the inner elongate member 11. When the inner elongate member 11 is rotated at milling speed in a clockwise manner, the integrated proximal gear rotates along with the rod while the free distal gear rotates in the opposite direction.

In other embodiments, the proximal gear member may be integrally connected to an outer hollow elongate member (such as a shaft) while the distal gear member is slidably received on an inner elongate member (such as a rod). When the outer shaft is rotated at milling speed in a clockwise manner, the integrated proximal gear rotates along with the shaft while the free distal gear rotates in the opposite direction.

In other embodiments, the distal gear member is integrally connected to the inner elongate member (such as a rod) while the proximal gear member is slidably received on the rod. When the inner rod is pulled proximally, the proximal gear will slide until it abuts the distal end of the outer elongate member (such as a shaft) and thereafter remain stationary, while the distal gear member will move proximally along the proximal movement of the rod, thereby reducing the distance between the gears and causing the abrading surface to rise away from the rod. When the inner rod of this embodiment is rotated at milling speed in a clockwise manner, the integrated distal gear member rotates along with the rod while the free proximal gear rotates in the opposite direction. In this case, the distal end of the inner rod will preferably form hub for preventing distal movement of the distal gear member Preferably, the device includes a stop means for securably connecting the abrading surface to the distal elongate member. In some embodiments, and now referring to FIG. 8b, the device includes a mounting member 71 located between the distance adjustment elements 7,17 along the connecting elongate member 15. In some embodiments, the mounting member is a pin which is sized so as to fit within a recess 73 in the adjacent surface 75 of the abrading element 30. In some embodiments, one end 77 of the pin has a laterally extending tongue 79, and the recess 73 has a lip 77, whereby the lip prevents the tongue from exiting the recess, thereby securably connecting the abrading element to the inner rod.

In some embodiments having a pair of opposed abrading elements, the mounting member can have two opposing ends or be a disc-shaped in order to secure each abrading element.

If a complex shape is desired, then use of a vibratory abrading surface is desirable.

Because rotation of one of the elongate members need not be considered in a vibratory system, a gear system need not be incorporated into the vibratory system. Accordingly, neither of the distance adjustment elements need be a gear member, and neither need be capable of movement independent of a elongate member. Rather, in a vibratory system, it is preferred that each distance adjustment element be integrally connected to its respective elongate member. Because there is no rotation in the vibratory system, the distance adjustment element need not be frustoconical, but rather can have any engagement surface which slidably engages to the adjacent to the abrading element.

Figure 9:
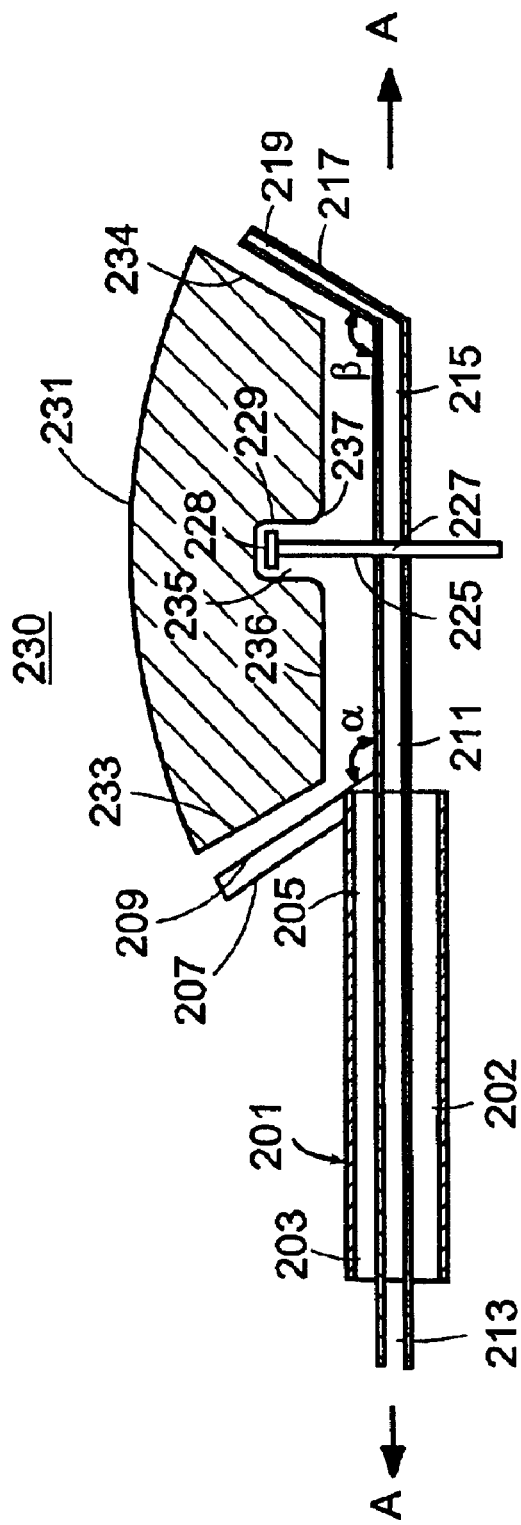
FIG. 9 is a cross-section of a vibratory device of the present invention.

In some vibratory embodiments, as in FIG. 9, the proximal distance adjustment element 207 is integrally connected to distal end of the outer elongate member 205 while the distal distance adjustment element 217 is integrally connected to the distal end 215 of the inner elongate member 211. In other vibratory embodiments, as in FIG. 5, the proximal distance adjustment element 307 is integrally connected to distal end 305 of the inner elongate member 305 while the distal distance adjustment element 317 is integrally connected to the distal end 315 of the outer elongate member 311.

The vibratory system can possess a stop means similar to the pin-recess means disclosed above for the rotary system. In other embodiments, the stop means in the vibratory system can be accomplished by providing a tongue-and-groove system upon the engagement surfaces of the gear and the abrading element.

Because the vibratory abrading element need not accommodate rotary motion, its abrading surface may possess any shape which forms the desired relief in the opposing endplate.

Generally, the vibratory abrading element will comprises an abrading surface and an angled engagement surface which functions as a sliding surface portion. The angled engagement portion may be continuous around the periphery of the abrading element (as in FIGS. 8a and 8b), or discontinuous (such as the two sliding surfaces portions provided in FIGS. 5 and 9). In many embodiments, the abrading surface is substantially convex. In some embodiment, the vibratory abrading element may further possess a securement surface having a recess therein for providing secure attachment to the distally extending elongate member.

Since each of the opposing vertebral endplates should be contoured, in preferred embodiments, the device comprises a pair of abrading elements for simultaneous contouring of the opposed endplates.

In some rotary embodiments having a mounting member, the second abrading element may comprise:
  i) a mounting member receiving surface having a recess therein for slidable reception of the second end of the mounting member,
  ii) an abrading surface selected to create a predetermined surface contour in one of the adjacent vertebral bodies as the abrading element is moved by the drive mechanism, and
  iii) a gear engagement surface adapted to engage both the first and second frustoconical gears.

In rotary embodiments, the required rotation of one of the elongate members may be accomplished by a drive mechanism including a motor. Preferably, the motor and rotating elongate member are connected by a gear mechanism.

In vibratory embodiments, the required vibration of one of the elongate members may be accomplished by a conventional vibration mechanism including a vibrator. Preferably, the vibrator and vibrating elongate member are integrally connected.

In some embodiments wherein the elongate members comprise an inner rod and an outer shaft, when the outer shaft is connected to either a drive mechanism or a vibration system, a handle may be provided at the proximal end of the inner rod in order to facilitate handling of the device in surgery. In other embodiments, when the inner rod is connected to either a drive mechanism or a vibration system, a handle is provided at the proximal end of the outer shaft for the same purpose.

Now referring to FIGS. 8a and 8b, there is provided a rotary device for preparing a space in the human spine to receive an insert between adjacent vertebral bodies, comprising:
a) a hollow shaft 1 having a bore 2, a proximal end 3 and a distal end 5 defining a first axis A;
b) a first frustoconical gear 7 disposed at the distal end of the hollow shaft and forming a first slidable engagement surface 9 which tapers distally at an angle $\alpha$ and has a plurality of teeth 10 formed thereon;
c) an elongate rod 11 having a proximal end 13 and a distal end 15, the rod being slidably movable within the hollow shaft along the first axis A;
d) a second frustoconical gear 17 disposed at the distal end 15 of the rod 11 and forming a second slidable engagement surface 19 which tapers proximally at the angle $\alpha$ and has a plurality of teeth 20 formed thereon; and
e) a first abrading element 30 comprising:
  i) an abrading surface 31 selected to create a predetermined surface contour in a vertebral body, and
  ii) a frustoconical surface 33 comprising first 34 and second 36 surface portions, each surface portion facing away from the abrading surface 31 and forming the angle $\alpha$ for slidable engagement with each of the gear engagement surfaces, and having teeth 35 formed thereon for geared engagement with the teeth of the gear engagement surfaces.

In use, the device of FIGS. 8a and 8b is first inserted into the disk space in its closed form. Because it is sized appropriately and is closed, its entrance does not destroy the lip of the vertebral endplate nor does it unduly stretch the ligaments. Next, the handle of the inner rod is pulled proximally, thereby bringing the distal gear to a more proximal position, and forcing the rotary abrading surface to a position farther from the inner rod. Inner rod is pulled proximally until the abrading surfaces reach the predetermined height which corresponds to the height of the implant. Next, the device is locked in order to fix the desired spacing and the power for the motor is turned on. The drive mechanism now forces the rotary abrading surfaces to turn at high speed, thereby creating a milling surface.

The device may be designed so as to be suitable for use in any or all of the cervical, thoracic or lumbar spine areas.

Now referring to FIG. 9, a vibratory device for preparing a space in the human spine to receive an insert between adjacent vertebral bodies, comprising:
a) a hollow shaft 201 having a bore 202, a proximal end 203 and a distal end 205 defining a first axis A;
b) a proximal distance adjustment element 207 extending from the distal end of the shaft and forming a first engagement surface 209 which tapers distally at an angle $\alpha$;
c) an elongate rod 211 having a proximal end 213 and a distal end 215, the rod being slidably movable within the hollow shaft along the first axis A;
d) a distal distance adjustment element 217 extending from the distal end of the rod and forming a second surface 219 which tapers proximally at the angle $\alpha$;

e) a mounting member 225 having a hole 227 for slidable reception upon elongate rod 211 and located upon elongate rod 211 between the first and distal distance adjustment elements, the mounting member 225 having an end 228 from which tongue 229 laterally extends, and f) a first abrading element 230 comprising:

i) an abrading surface 231 selected to create a predetermined surface contour in a vertebral body, and ii) a proximal surface portion 233 disposed at the angle a for slidable engagement with the first engagement surface of the proximal distance adjustment element, iii) a distal surface portion 234 disposed at the angle α for slidable engagement with the second engagement surface of the distal distance adjustment element, and iv) a surface 236 disposed between the first and second engagement surfaces and having a recess 235 for the slidable reception of mounting member, and further having a lip 237 around recess 235 for retaining tongue 229 within the recess.

Now referring to FIG. 5, a vibratory device for preparing a space in the human spine to receive an insert between adjacent vertebral bodies, comprising:

a) an elongate rod 301 having a proximal end 303 and a distal end 305 defining a first axis A;

b) a proximal distance adjustment element 307 extending from the distal end of the shaft and forming a first slidable engagement surface 309 which tapers distally at an angle α, the first slidable engagement surface having a first groove 310 therein disposed at the angle α;

c) a hollow shaft 311 having a bore 302, a proximal end 313, a distal end 315, and a elongate slot 316 along axis A, the rod 301 being movable within the hollow shaft along the first axis A and proximal distance adjustment element 307 being movable within slot 316 along the first axis A;

d) a distal distance adjustment element 317 extending from the distal end of the shaft 311 and forming a second slidable engagement surface 319 which tapers proximally at an angle α, the second slidable engagement surface having a second groove 318 therein disposed at the angle α; and e) a first abrading element 330 comprising:

i) an abrading surface 331 selected to create a predetermined surface contour in a vertebral body, ii) a proximal surface portion 333 disposed between the abrading surface and the proximal distance adjustment element at the angle α for slidable engagement with the first slidable engagement surface of the proximal distance adjustment element and having a first stop 335 extending from the proximal surface portion for slidable reception within first groove 310, iii) a distal distance adjustment element engagement surface 334 disposed between the abrading surface and the distal distance adjustment element at the angle α for slidable engagement with the second slidable engagement surface of the distal distance adjustment element and having a second stop 337 extending from the second surface for slidable reception within second groove 318.

Typically, the elongate members, distance adjustment elements and mounting members can be made out of any material commonly used in instruments used spinal fusion operations, including hardened stainless steel alloys, such as Custom 455 Stainless, available from Carpenter Specialty Alloys of Wyomissing, Pa. Each of these components should be sterilizable. The abrading surfaces can be made from metals such as stainless steel (preferably for rotary devices) or conventional abrasives composites (preferably for rotary devices or vibratory devices).

As noted above, the tension on ligaments produced by the extension of the opposing vertebrae is often an important factor in interbody devices. However, present methods for determining this tension appear to be limited to merely inserting an instrument between the opposing bodies and manually appreciating the feeling of tightness. There appears to be no objective measure for measuring tension.

Because the height of the device of the present invention is changeable in situ, and the device may also be used to measure the tension produced in the ligaments surrounding disc space when the height is so increased.

Therefore, in accordance with the present invention, there is provided a method of measuring a tension in a disc space, comprising the steps of:

a) removing at least a portion of an intervertebral disc to create a disc space having an endplate, b) inserting into the disc space a device comprising a first abrading element so that the first abrading element faces but does not contact the endplate, c) contacting the first abrading surface with the endplate, and d) measuring a force required to maintain the contact between the abrading surface and the endplate.

U.S. Pat. No. 6,083,228 is hereby incorporated by reference herein.

I claim:

1. A device for preparing a space in the human spine to receive an insert between adjacent vertebral bodies, comprising:

a) a first abrading element comprising:

i) a first abrading surface shaped to create a first predetermined surface contour in a vertebral body endplate, ii) a first surface portion facing away from the first abrading surface, and iii) a second surface portion facing away from the first abrading surface, b) a first distance adjustment element having a first sliding surface contacting the first surface portion for slidable engagement therewith, and c) a second distance adjustment element having a second sliding surface contacting the second surface portion for slidable engagement therewith, and wherein the first distance adjustment element further comprises a first inner face, the second distance adjustment element further comprises a second inner face, and wherein the first inner face opposes the second inner face.

2. The device of claim 1 wherein the first sliding surface opposes the second sliding surface.

3. The device of claim 1 wherein the first distance adjustment element further comprises a first outer face, the second distance adjustment element further comprises a second outer face, and wherein the first outer face faces away from the second outer face.

4. The device of claim 3 wherein the first distance adjustment element further comprises a first hole traversing the inner and outer faces thereof.

5. The device of claim 3 further comprising a first elongate member having a proximal portion and a distal portion, and forming a hollow shaft, wherein the distal portion contacts the first outer face.

6. The device of claim 5 wherein the first distance adjustment element further comprises a first hole traversing the inner and outer faces thereof, the device further comprising a second elongate member extending through the hollow shaft and the first hole.

7. The device of claim 6 wherein the second elongate member is slidably disposed in the first hole.

8. The device of claim 3 wherein the second distance adjustment element further comprises a second hole traversing the inner and outer faces thereof.

9. The device of claim 8 wherein the first distance adjustment element further comprises a first hole traversing the inner and outer faces thereof, and wherein the first and second holes are co-axial and the second elongate member slidably extends through each of the first and second holes.

10. The device of claim 3, further comprising a first elongate member having a proximal portion and a distal portion, wherein the first distance adjustment element is integral with the distal portion of the first elongate member.

11. The device of claim 10 wherein the first elongate member is a hollow shaft and the distal portion thereof forms a first hole through the first distance adjustment member.

12. The device of claim 11 further comprising a second elongate member having a proximal end and a distal end, wherein the second elongate member is co-axial within the first elongate member.

13. The device of claim 12 wherein the second elongate member is slidably disposed within the first elongate member.

14. The device of claim 12 wherein the distal end of the second elongate member is integral with the second distance adjustment element.

15. The device of claim 3 further comprising first and second elongate members, wherein the second elongate member is a hollow shaft, and the first elongate member is disposed therein, wherein the first elongate member is integral with the first distance adjustment member, and wherein the second elongate member further comprises a slot through which the first distance adjustment member extends.

16. The device of claim 15, further comprising a stop extending from the first surface portion of the first abrading element.

17. The device of claim 3 wherein the first distance adjustment element further comprises a first hole traversing the inner and outer faces thereof and having a first inner thread.

18. The device of claim 17 comprising a first elongate member having an outer thread, wherein the first elongate member threadably extends through the first hole.

19. The device of claim 18 wherein the second distance adjustment element further comprises a second hole traversing the inner and outer faces thereof and having a second inner thread.

20. The device of claim 17 wherein the mounting member is a disc.

21. The device of claim 3 wherein the first distance adjustment element comprises a plurality of teeth formed on the sliding surface thereof.

22. The device of claim 21 wherein the first surface portion of the first abrading element has a plurality of teeth formed thereon for rotary engagement with a plurality of teeth of a frustoconcial gear.

23. The device of claim 21 wherein the teeth of the first distance adjustment element comprise radial grooves.

24. The device of claim 23 further comprising a first elongate member, wherein the first distance adjustment element comprises a centrally disposed throughhole, and the first elongate member is disposed within the throughhole so that the first distance adjustment element is freely rotational upon the first elongate member.

25. The device of claim 3 wherein the first distance adjustment element further comprises a first hole traversing the inner and outer faces thereof, the second distance adjustment element further comprises a second hole traversing the inner and outer faces thereof, wherein the device further comprises:

d) a first elongate member extending through the first and second holes, and e) a mounting member located upon the first elongate member between the first and second inner faces, the mounting member having an end from which a tongue laterally extends, wherein the abrading element further comprises:

iv) a surface disposed between the sliding surfaces and having a recess for the slidable reception of the mounting member, and a lip around the recess for retaining the tongue within the recess, and wherein the mounting member is disposed within the recess.

26. The device of claim 25 further comprising;

f) a compression spring disposed between the tongue of the mounting member and the lip of the abrading element.

27. The device of claim 25 wherein the mounting member is a elongate rod.

28. The device of claim 1 wherein the first distance adjustment element further comprises a third sliding surface facing away from the first sliding surface, and the second distance adjustment element further comprises a fourth sliding surface facing away from the second sliding surface.

29. The device of claim 28 wherein the third sliding surface opposes the fourth sliding surface.

30. The device of claim 28 further comprising:

a) a second abrading element comprising:

i) a second abrading surface shaped to create a second predetermined surface contour in a vertebral body endplate, and ii) a third surface portion facing away from the second abrading surface, and iii) a fourth surface portion facing away from the second abrading surface, wherein the third surface portion contacts the third sliding surface for slidable engagement therewith, and wherein the fourth surface portion contacts the fourth sliding surface for slidable engagement therewith.

31. The device of claim 30 wherein the first distance adjustment element and the distal portion of the first elongate member are integral.

32. The device of claim 1 wherein the first sliding surface of the first distance adjustment element faces away from the second sliding surface of the second distance adjustment element.

33. The device of claim 1 wherein further comprising a first elongate member comprising a hollow shaft, and a second elongate member axially disposed in and axially movable within the hollow shaft, wherein the second elongate member has teeth.

34. The device of claim 1 wherein the first and second surface portions of the first abrading element form a frustoconical surface portion.

35. The device of claim 34 wherein the frustoconical surface portion of the first abrading element comprises teeth.

36. The device of claim 34 wherein the frustoconical surface portion of the first abrading element forms a total angle of between 30 and 60 degrees.

37. The device claim 1 wherein the abrading surface is substantially convex.

38. The device of claim 1 wherein the abrading surface is complex.

39. The device of claim 1 wherein the abrading surface comprises at least one feature.

40. The device of claim 1 wherein the outer abrading surface comprises a coated abrasive.

41. The device of claim 1 further comprising: d) means for vibrating the abrading surface.

42. The device of claim 41 wherein each distance adjustment element comprises a hole extending through the inner and outer faces thereof, and wherein the means for vibrating the abrading surface comprises an elongate member extending through the holes and having a protrusion extending therefrom, the protrusion located between the inner faces of the distance adjustment members and having a length sufficient to periodically contact the abrading element during rotation.

43. The device of claim 42 further comprises a motor mechanically connected to the elongate member for spinning the member.

44. The device of claim 1 further comprising d) means for measuring tension between the abrading elements.

45. A method for preparing a space in the human spine to receive an insert between adjacent vertebral endplates, comprising:
- a) removing at least a portion of an interverterbal disc to form a disc space,
- b) inserting into the disc space a device for preparing a space in the human spine to receive an insert between adjacent vertebral bodies, comprising:
  a first abrading element comprising:
  - i) a first abrading surface shaped to create a first predetermined surface contour in a vertebral body endplate,
  - ii) a first surface portion facing away from the first abrading surface, and
  - iii) a second surface portion facing away from the first abrading surface,
  a first distance adjustment element having a first sliding surface contacting the first surface portion for slidable engagement therewith, and
  a second distance adjustment element having a second sliding surface contacting the second surface portion for slidable engagement therewith, and
- c) contacting the first abrading surface with at least one vertebral body endplate.

46. A method of measuring a tension in a disc space, comprising the steps of:
- a) removing at least a portion of an intervertebral disc to create a disc space having an endplate,
- b) inserting into the disc space a device comprising a first abrading element so that the first abrading element faces but does not contact the endplate,
- c) contacting the first abrading element with the endplate, and
- d) measuring a force required to maintain the contact between the abrading element and the endplate.

* * * * *